(12) United States Patent
Kirkpatrick et al.

(10) Patent No.: US 7,236,248 B2
(45) Date of Patent: Jun. 26, 2007

(54) OPTICAL PHYTOPLANKTON DISCRIMINATOR

(75) Inventors: Gary J. Kirkpatrick, Sarasota, FL (US); James R. Hillier, Sarasota, FL (US)

(73) Assignee: Mote Marine Laboratory, Sarasota, FL (US)

( * ) Notice: Subject to any disclaimer, the term of this patent is extended or adjusted under 35 U.S.C. 154(b) by 33 days.

(21) Appl. No.: 11/316,312

(22) Filed: Dec. 21, 2005

(65) Prior Publication Data

US 2006/0132762 A1 Jun. 22, 2006

Related U.S. Application Data

(60) Provisional application No. 60/638,789, filed on Dec. 22, 2004.

(51) Int. Cl.
*G01N 21/59* (2006.01)
(52) U.S. Cl. .................... 356/435; 356/436; 356/440
(58) Field of Classification Search ................ 356/433, 356/434, 435, 436, 440, 246
See application file for complete search history.

(56) References Cited

U.S. PATENT DOCUMENTS

| | | | | |
|---|---|---|---|---|
| 3,200,700 A | * | 8/1965 | Topol | 356/341 |
| 4,063,094 A | * | 12/1977 | Schuman | 250/338.1 |
| 4,111,560 A | * | 9/1978 | Jolanki et al. | 356/434 |
| 4,950,610 A | * | 8/1990 | Tittle | 356/435 |
| 6,020,207 A | | 2/2000 | Liu | |
| 6,603,556 B2 | | 8/2003 | Belz et al. | |

OTHER PUBLICATIONS

Steidinger, K. A., Burklew, M. A. and Ingle, R. M., "The effects of *Gymnodinium breve*toxin on estuarine animals", In: D. F. Martine and G. M. Padilla (Editors), Marine pharmacology: Action of marine biotoxins at the cellular level, Academic., pp. 179-202 (1973).

Garver, S.A., D.A. Siegel and G.B. Mitchell, "Variability in near-surface particulate absorption spectra: What can an ocean color imager see?", Limnol. Oceanogr. 39, 1349-1367 (1994).

Millie et al., "Relating photosynthetic pigments and in vivo optical density spectra to irradiance for the Florida red-tide dinoflagellate *Gymnodinium breve*", Marine Ecology Progress Series, vol. 120, pp. 65-75 (1995).

Boesch, D.F., D.M. Anderson, R.A. Horner, S.E. Shumway, P.A. Tester and T.E. Whitledge, "Harmful Algal Blooms in Coastal Waters: Options for Prevention", Control and Mitigation. NOAA Coastal Ocean Program Decision Analysis Series No. 10. NOAA Coastal Ocean Office, Silver Spring, MD. 61 pp. (1997).

(Continued)

*Primary Examiner*—Richard A. Rosenberger
(74) *Attorney, Agent, or Firm*—IPLM Group, P.A.

(57) ABSTRACT

An apparatus and method for analyzing liquid samples employs first and second bidirectional ports that permit liquids to be introduced to first and second liquid waveguide capillary cells at the same time. The direction of liquid flow through the apparatus and roles of components may be reversed to prevent or overcome obstruction by particulates and other debris. The apparatus and method can detect and map colored dissolved organic matter and can detect, discriminate and map algal species or algal blooms including red tide in an automated, unattended manner within large aquatic systems.

20 Claims, 6 Drawing Sheets

OTHER PUBLICATIONS

Millie et al., "Detection of harmful algal blooms using photopigments and absorption signatures: A case study of the Florida red tide dinoflagellate, *Gymnodinium breve*", Limnol. Oceanorg., 42 (5, part 2) (1971), pp. 1240-1251.

E. J. D'Sa et al., "Determining optical absorption of colored dissolved organic matter in seawater with a liquid capillary waveguide", Limnol. Oceanogr. 44, 1142-1148 (1999).

Lohrenz et al., "Microphotometric Assessment of Spectral Absorption and Its Potential Application for Characterization of Harmful, Algal Species", J. Phycol., 35, pp. 1438-1446 (1999).

Schofield et al., "Optical Monitoring and Forecasting Systems for Harmful Algal Blooms: Possibility or Pipe Dream?", J. Phycol., 35, pp. 1477-1496 (1999).

Kirkpatrick, G.J., D.F. Millie, M.A. Moline, and O. Schofield, "Optical discrimination of a phytoplankton species in natural mixed populations", Limnol. Oceanogr., 45(2), pp. 467-471, (2000).

Millie et al., "Using absorbance and fluorescence spectra to discriminate microalgae", Eur. J. Phycol., 37, pp. 313-322 (2002).

Kirkpatrick et al., "Continuous hyperspectral absorption measurements of colored dissolved organic material in aquatic systems", Applied Optics, 42, 33, 6564-68 (Nov. 20, 2003).

Sellner et al., "Harmful algal blooms: causes, impacts and detection", J Ind Microbiol Biotechnol, 30, pp. 383-406 (2003).

Stumpf et al., "Monitoring *Karenia brevis* blooms in the Gulf of Mexico using satellite ocean color imagery and other data", Harmful Algae, 2, pp. 147-160 (2003).

Schofield et al., "Inversion of spectral absorption in the optically complex coastal waters of the Mid-Atlantic Bight", Journal of Geophysical Research, vol. 109, C12S04, pp. 1-12 (2004).

Bissett et al., "Predicting the optical properties of the West Florida Shelf: resolving the potential impacts of a terrestrial boundary condition on the distribution of colored dissolved and particulate matter", Marine Chemistry 95, pp. 199-233 (2005).

* cited by examiner

OPTICAL PHYTOPLANKTON DISCRIMINATOR

CROSS REFERENCE TO RELATED APPLICATION

This application claims priority to Provisional Application Ser. No. 60/638,789, filed Dec. 22, 2004 and entitled "Optical Phytoplankton Discriminator", the disclosure of which is incorporated herein by reference.

FIELD OF THE INVENTION

This invention relates to the detection of algal species and colored dissolved organic matter in water, to the identification of such algal species, and to the detection and measurement of algal blooms.

BACKGROUND

Blooms of the toxic dinoflagellate, *Karenia brevis*, are a frequent occurrence off the coast of Florida in the Gulf of Mexico. Although such blooms generally develop and terminate offshore, wind and currents can concentrate assemblages in nearshore waters, creating a condition referred to locally and elsewhere as "red tide". Harmful algal blooms pose a threat and efforts to reduce or eliminate their negative impacts and consequences are necessary. In the Gulf of Mexico, toxic blooms of *K. brevis* regularly lead to untimely restrictions on commercial and recreational shellfish harvesting and deleterious effects on tourism and public health. Toxic blooms of *K. brevis* are generally detected by visual confirmation (e.g., water discoloration and fish kills), illness to shellfish consumers, or human respiratory irritation with actual toxicity verified through time-consuming chemical analyses for brevetoxins within shellfish samples and mouse bioassays. Currently, biological monitoring programs primarily rely on microscope-based cell enumeration and gross measurements of a biochemical parameter, such as chlorophyll-a concentration, for characterizing algal species and estimating biomass. Existing methods can be slow, labor intensive, intermittent, and do not always provide timely or accurate measurements. Developing optical detection methods for discriminating particular phytoplankton species in mixed phytoplankton assemblages has long been a goal of aquatic scientists. Phytoplankton pigment and light absorbance analyses could be incorporated into coastal monitoring programs and thus provide an effective and alternative means for monitoring *K. brevis*. Mitigation of some of the harmful effects resulting from toxic blooms of *K. brevis* could be achieved by early detection of this species in mixed phytoplankton communities.

The majority of organic carbon in the oceans is present as dissolved organic matter ("DOM"). A significant proportion of DOM has color (abbreviated "CDOM"), and is often present in concentrations sufficient to affect the color of lakes, estuaries, and near-shore coastal water. Due to the presence of CDOM in waters where phytoplankton assemblages occur, baseline CDOM measurements of water in the area are necessary. Additionally, mapping the distribution of CDOM including its time-space variability is central to understanding global carbon cycles. Characterizing CDOM variability is problematic because standard spectrometric methods for determining CDOM concentration are laborious and susceptible to methodological biases. For example, the collection and storage of discrete water samples for analysis in the laboratory often introduces artifacts such as contamination and photolysis. Also, the numerous steps required to conduct these analyses limit the number of samples that can be collected and effectively analyzed.

The use of liquid waveguide capillary cell ("LWCC") technology for CDOM absorption measurements has been described in E. J. D'Sa et al., "Determining optical absorption of colored dissolved organic matter in seawater with a liquid capillary waveguide", Limnol. Oceanogr. 44, 1142–1148 (1999). A near-continuous automated LWCC analytical technique for mapping CDOM distribution in an aquatic system is described in Kirkpatrick et al., "Continuous hyperspectral absorption measurements of colored dissolved organic material in aquatic systems", Applied Optics, 42, 33, 6564–68 (20 Nov. 2003). Devices employing an LWCC are also described in U.S. Pat. Nos. 6,020,207 and 6,603,556 B2.

SUMMARY OF THE INVENTION

During intense algal blooms, LWCC analytical devices and their associated components may require frequent cleaning. Instrument drift and local water changes may also necessitate sensor recalibration or more frequent reference spectrum collection. The above-mentioned Kirkpatrick et al. paper describes several measures to deal with these problems, including the use of a prefilter and a high water flow rate across the prefilter inlet with the majority of filtrate going to waste rather than through the instrument, and the use of two LWCCs operated on an alternating schedule to reduce gaps in the data record caused by cleaning and new reference spectrum collection.

The present invention provides an improved apparatus and detection method for measuring algal blooms in liquids (e.g., in seawater or fresh water) and for discriminating harmful algal species in such blooms. In one aspect the invention provides an apparatus for analyzing liquid samples, the apparatus comprising:
  (a) first and second bidirectional ports for providing liquid samples to the apparatus and discharging liquid samples from the apparatus,
  (b) first and second liquid waveguide capillary cells in fluid communication with the first and second ports and arranged to analyze different liquid samples at the same time,
  (c) at least one light source and at least one spectrometer in optical communication with the first and second cells, and
  (d) a bidirectional pump or control arranged to flow samples in alternate directions through the first and second ports.

In a preferred embodiment of the disclosed apparatus the first and second ports are each in fluid communication with one liquid waveguide capillary cell and in filtered fluid communication with another liquid waveguide capillary cell. In additional embodiments the cells are interchangeable, are arranged in series, or are arranged in parallel. In another preferred embodiment the disclosed apparatus can carry out continuous sample analysis.

In another aspect the invention provides a method for analyzing liquid samples, the method comprising:
  (a) obtaining one or more liquid samples through a first bidirectional port,
  (b) flowing the sample(s) into two or more liquid waveguide capillary cells,
  (c) spectroscopically analyzing the contents of the cells,
  (d) discharging the sample(s) through a second bidirectional port, (e) reversing the sample flow direction through the first and second ports, and (f) repeating steps (b) and (c) using such reversed sample flow.

In further embodiments of the disclosed method the first and second ports are each in fluid communication with one liquid waveguide capillary cell and in filtered fluid communication with another liquid waveguide capillary cell; or the cells are interchangeable, or are arranged in series, or are arranged in parallel; or the samples are analyzed continuously.

The disclosed bidirectional ports facilitate automatic cleansing of debris that might otherwise block the flow of liquid through the disclosed apparatus. The disclosed apparatus and method may provide more accurate, more frequent or more reliable detection, mapping or tracking of algal blooms, algal species and CDOM characteristics, including time and space variability, in a real-time or unattended manner.

BRIEF DESCRIPTION OF THE DRAWINGS

The present invention will be better understood by way of the specific embodiments shown in the following figures, the purpose of which is to illustrate the invention rather than to limit its scope.

Like reference symbols in the various figures of the drawing indicate like elements. The elements in the drawing are not to scale.

DETAILED DESCRIPTION

Figure 1:
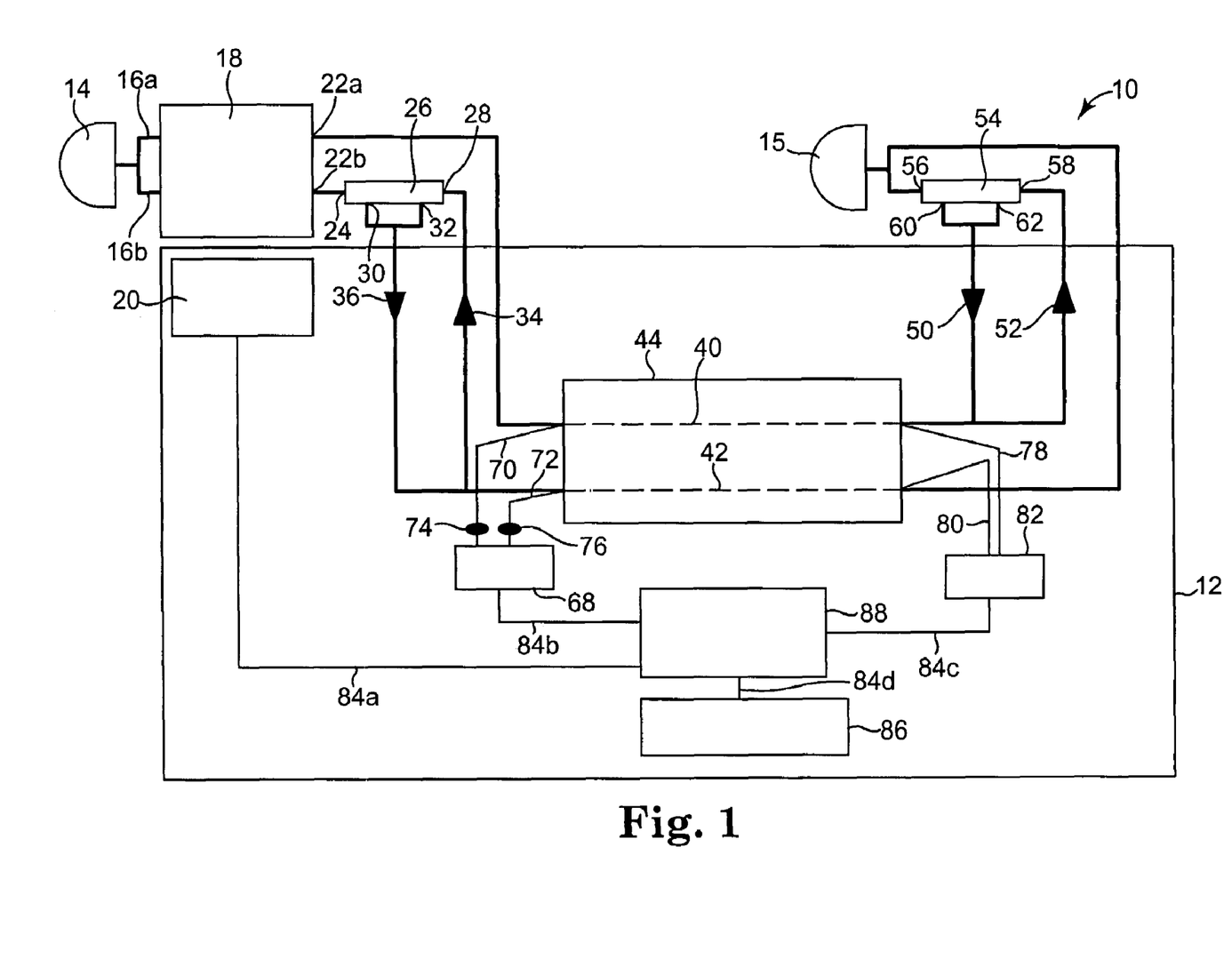
FIG. 1 is a schematic view of an Optical Phytoplankton Discriminator apparatus with parallel-connected LWCCs.

Referring to FIG. 1, Optical Phytoplankton Discriminator apparatus 10 includes instrument housing 12 containing most of the components in the apparatus. Several components that may need more frequent cleaning or replacement are located outside housing 12. Liquids enter and leave apparatus 10 via first bidirectional port 14 and second bidirectional port 15. Port 14 is connected via suitable diameter tubing (e.g., 0.5 mm inside diameter tubing) and a suitable tubing wye to fittings 16a and 16b of dual channel bidirectional gear pump 18 and thence through fittings 22a and 22b to the remaining liquid circuits in apparatus 10. Pump 18 contains three planetary mesh gears (not shown in FIG. 1) arranged so that a central drive gear drives a first orbital gear that moves liquid in a first pump channel between fitting 16a and fitting 22a, and drives a second orbital gear that moves liquid (flowing in the opposite direction through pump 18) in a second pump channel between fitting 16b and fitting 22b. Pump 18 is magnetically coupled to drive motor 24 located inside housing 10. Motor 24 can drive pump 18 in either direction so that ports 15 and 16 respectively serve as liquid inlet and outlet or as liquid outlet and inlet for apparatus 10. When the liquid flow direction is such that port 14 is serving as an inlet, liquid exits pump 18 via fittings 22a and 22b. Fitting 22a is connected via tubing to LWCC 40 located inside light-proof housing 44. Fitting 22b is connected via tubing to fitting 24 of filter 26.

Figure 2:
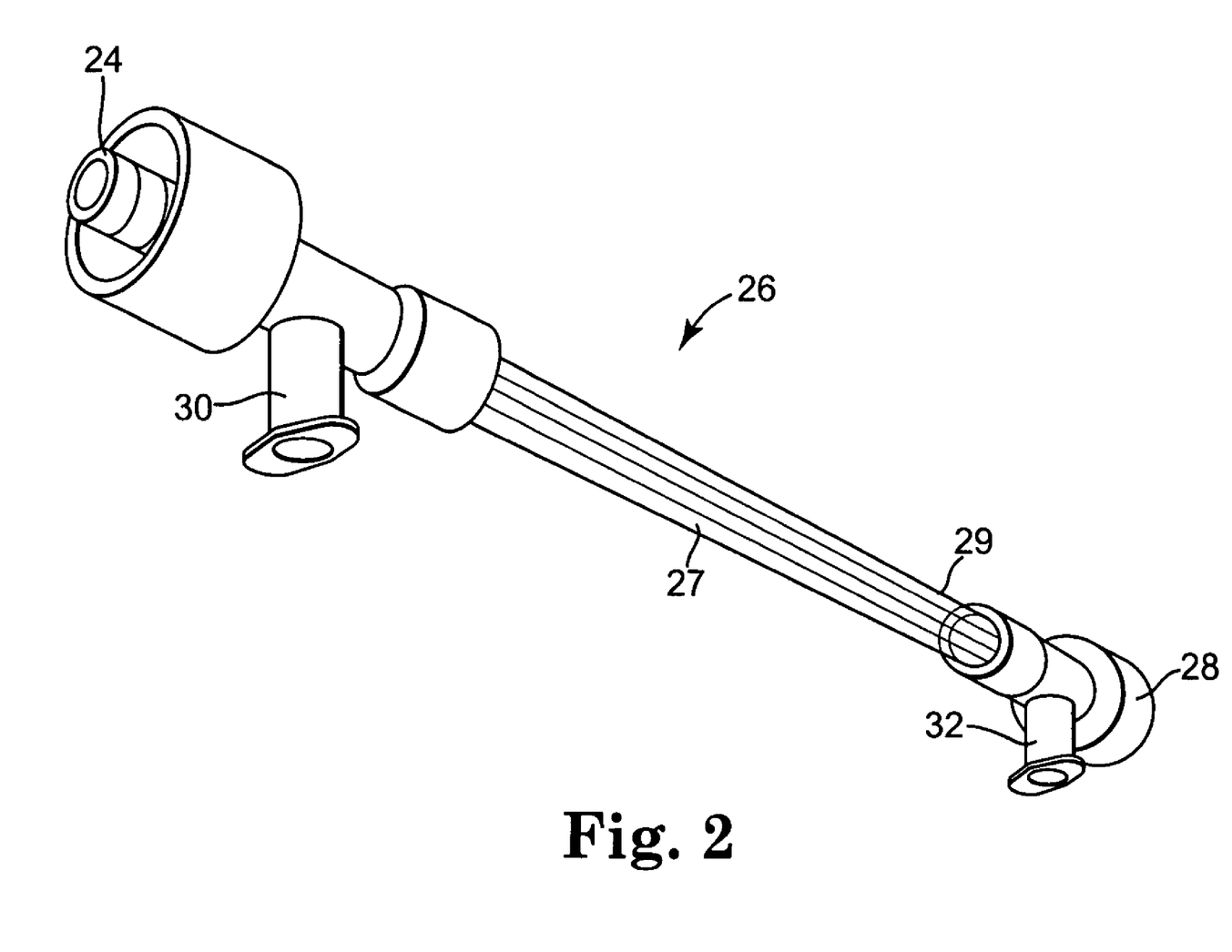
FIG. 2 is a perspective view of a filter that may be used in the FIG. 1 apparatus.

Filter 26 (which may for example be a MICROKROS™ cross-flow filter module from Spectrum Laboratories, Inc.) is shown in perspective view in FIG. 2. Liquid can flow between fittings 24 and 26 through hollow fibers 27 disposed in housing 29. Fibers 27 have porous sidewalls through which filtered liquid (filtrate) passes when exiting filter 26. Thus when unfiltered liquid flows into fitting 24 and suitable back pressure exists at fitting 28, filtrate will exit through fittings 30 and 32.

Referring again to FIG. 1, check valve 34 can provide such back pressure and prevent liquid from flowing out of filter 26 via fitting 28 when the liquid flow direction is such that port 14 is serving as an inlet. At the same time, filtrate exits filter 26 through fittings 30 and 32, then passes through a suitable tubing wye, check valve 36 and thence into LWCC 42. Meanwhile, unfiltered (or, if any liquid screening or other prefiltration has taken place in port 14, less finely filtered) liquid travels from pump fitting 22a to LWCC 40. Liquid from LWCC 40 can exit apparatus 10 by passing through check valve 52 into fitting 58 and thence through filter 54, fitting 56, a suitable tubing wye, and port 15. Filter 54 may for example be a hollow fiber filter like filter 26. Filter 54 may if desired be different from filter 26. For example, filter 54 may be sized to pass larger or smaller particles than filter 26, thereby permitting analysis of differently sized particles, or different organisms, in each liquid flow direction through apparatus 10. Meanwhile, liquid from LWCC 42 can exit apparatus 10 by passing through suitable tubing and the above-mentioned tubing wye and thence through port 15.

Accordingly, when the liquid flow direction is such that port 14 is serving as an inlet, the FIG. 2 embodiment supplies an unfiltered (or less finely filtered) liquid sample to LWCC 40. This liquid sample may for example contain CDOM, organisms and other particulate matter, and may be referred to as the "discriminate" sample. Simultaneously, a filtered (or more finely filtered) liquid sample is supplied to LWCC 42. This latter liquid sample may for example contain CDOM but no or few algal species and may be referred to as a locally-obtained "reference" CDOM sample. Reference CDOM measurements will vary depending on CDOM concentration at each sampling site. Desirably, a further reference spectrum will have earlier been obtained using pure seawater collected far offshore away from terrestrial sources of CDOM, or using filtered seawater collected from an open ocean site where CDOM content may be at a minimum. This earlier reference spectrum may be referred to as the CDOM baseline. The CDOM baseline will be constant whereas the CDOM reference will vary based on the site where the local sample was taken. The locally measured reference CDOM sample is compared to the CDOM baseline spectrum to determine a CDOM absorption spectrum. The CDOM absorption spectrum may in turn be used as a reference spectrum for determining a particle absorbance spectra and discriminating algal groups in an unfiltered or less finely filtered sample. The particle absorbance spectrum may for example be used to calculate the logarithm of the ratio of the CDOM reference sample transmitted spectrum to the particulate light transmitted spectrum using an algorithm such as those described below. This effectively eliminates CDOM from the resultant spectrum and leaves only light absorbance due to undissolved particles that passed through the filter.

After apparatus 10 has been in operation for a time with port 14 serving as an inlet, large particles and other debris may obstruct one or more parts of apparatus 10. For example, debris may obstruct port 14, may be carried into filter 26 and clog or otherwise obstruct the hollow ends of fibers 27 near fitting 24, or may be carried into LWCC 40. The onset of such obstruction may be detected using a variety of measures such as by monitoring a suitable pressure drop transducer (not shown in FIG. 2) located in an appropriate part of the liquid flow circuit. The onset of such obstruction may also be forecasted by measuring elapsed operating time, integrating a detected species count, or through any other suitable scheduling measure. Meanwhile, while port 14 has served as an inlet, the flow of liquid from LWCC 40 through filter 54 and port 15, and the flow of liquid from LWCC 42 through port 15, will have helped flush away particles that might otherwise have obstructed port 15 or filter 54. Once obstruction has taken place (or is forecasted to take place) in apparatus 10, the flow of liquid may be reversed by reversing motor 20. When such reversal takes place, the roles of ports 14 and 15, filters 26 and 54, and LWCCs 40 and 42 will also be reversed. Liquid will flow into apparatus 10 through port 15. Check valve 52 will provide back pressure at fitting 58. Filtrate will flow from filter 54 through fittings 60 and 62 and check valve 50 to LWCC 40, then exit apparatus 10 by passing through fitting 22a, pump 18, fitting 16a and port 14. Meanwhile, unfiltered (or less finely filtered) liquid will flow from port 15 to LWCC 42, and then will exit apparatus 10 by passing through check valve 34 into fitting 28 and thence through filter 26, fittings 24 and 22b, pump 18, fitting 16b and port 14. The flow of liquid from LWCC 42 through filter 26, and the flow of liquid from LWCC 40 through port 14, will help flush away particles that might otherwise obstruct port 14 or filter 26. The above-described flow reversal may be repeated again and again as needed so that apparatus 10 will remain unobstructed by debris, or will recover normal operation if it becomes obstructed.

Accordingly, by periodically reversing the direction of liquid flow through ports 14 and 15, filters 26 and 54, and LWCCs 40 and 42, large particles and other debris can be flushed away and discouraged or prevented from clogging or otherwise obstructing apparatus 10. Meanwhile, the flow of liquid through LWCCs 40 and 42 can take place on an essentially continuous or semi-continuous basis while spectral measurements are obtained.

If desired pump 18 and motor 20 may be eliminated and the flow of liquid through apparatus 10 may be controllably reversed using other measures. For example, when installed in a vessel, ports 14 and 15 may be oriented so that one port is always exposed to higher water pressure and the connections to the two ports may be reversed using a suitable valve, by exchanging the tubing connections at each port, or through any other convenient changeover measure. Ports 14 and 15 may also or instead be mounted in movable fashion on a suitable through-hull fitting capable of alternately exposing one or the other of port 14 and port 15 to higher water pressure relative to the other port (for example, by alternately turning port 14 or port 15 to face towards or more towards the bow).

The FIG. 1 apparatus thus simultaneously supplies different liquid samples to two LWCCs using bidirectional ports and a filter at each such port. Liquid samples are drawn into the apparatus through a first port and are directed either through a first filter and a first LWCC and out of the apparatus through a second port, or are directed into a second LWCC and then through a second filter and out of the apparatus through the second port. The roles of these first and second components are reversed when the direction of liquid flow is reversed. For example, the resulting role and flow reversal can exchange an LWCC measuring a CDOM reference with an LWCC measuring a discriminate sample, while changing the flow direction in each LWCC. Such role and flow reversal can automatically clean intake ports, tubing, and LWCCs, and can prevent such components from becoming clogged or otherwise impaired by particulate matter or other debris.

Referring again to FIG. 1, liquid discriminate sample analysis may be carried out by illuminating LWCCs 40 and 42 with a suitable energy source and analyzing light transmission through each LWCC. The light source 68 may be any suitable source of ultraviolet, visible or infrared light. For example, light source 68 may incorporate a deuterium lamp and a tungsten lamp modified with a color correction filter (not shown in FIG. 1) to balance the light emitted. For example, the color correction filter may employ stacked FG3 and BG26 filters (both from CVI Laser Corporation) so that the lamps transmit wavelengths from 320 nm to 840 nm. The resulting light may be supplied in optical communication with LWCCs 40 and 42 in any convenient fashion, such as through optical fibers 70 and 72. Electromechanical shutters 74 and 76 may be positioned between light source 68 and optical fibers 70 and 72 so that light will enter LWCCs 40 and 42 in intermittent (e.g., alternating) fashion. Light transmitted through LWCCs 40 and 42 can be collected in any convenient fashion for analysis using one or more spectrometers such as spectrometer 82. For example, such light may be collected using optical fibers 78 and 80, filtered if need be through suitable optical filters (not shown in FIG. 1) and optically communicated to spectrometer 82. Spectrometer 82 may for example be a USB2000fiber optic spectrometer from Ocean Optics, Inc. calibrated to detect transmitted light over a wavelength range from ultraviolet to near infrared (e.g., from 250 nanometers to 850 nanometers). Electrical control lines 84a, 84b, 84c and 84d can connect pump motor 20, light source 68, spectrometer 82 and microcomputer 86 with power control circuitry 88. Additional electrical control lines (not shown in FIG. 1) may be used to operate shutters 74 and 76, or appropriate signal detection circuitry may for example be used to determine when shutters 74 and 76 are open. Microcomputer 86 may for example record data; control pump 18, light source 68 and spectrometer 82; or perform calculations. After sampling is complete, the data or calculations may be stored in onboard computer memory or downloaded from apparatus 10 through a suitable communications scheme such as a wireless or wired link and a serial communications protocol.

Figure 3:
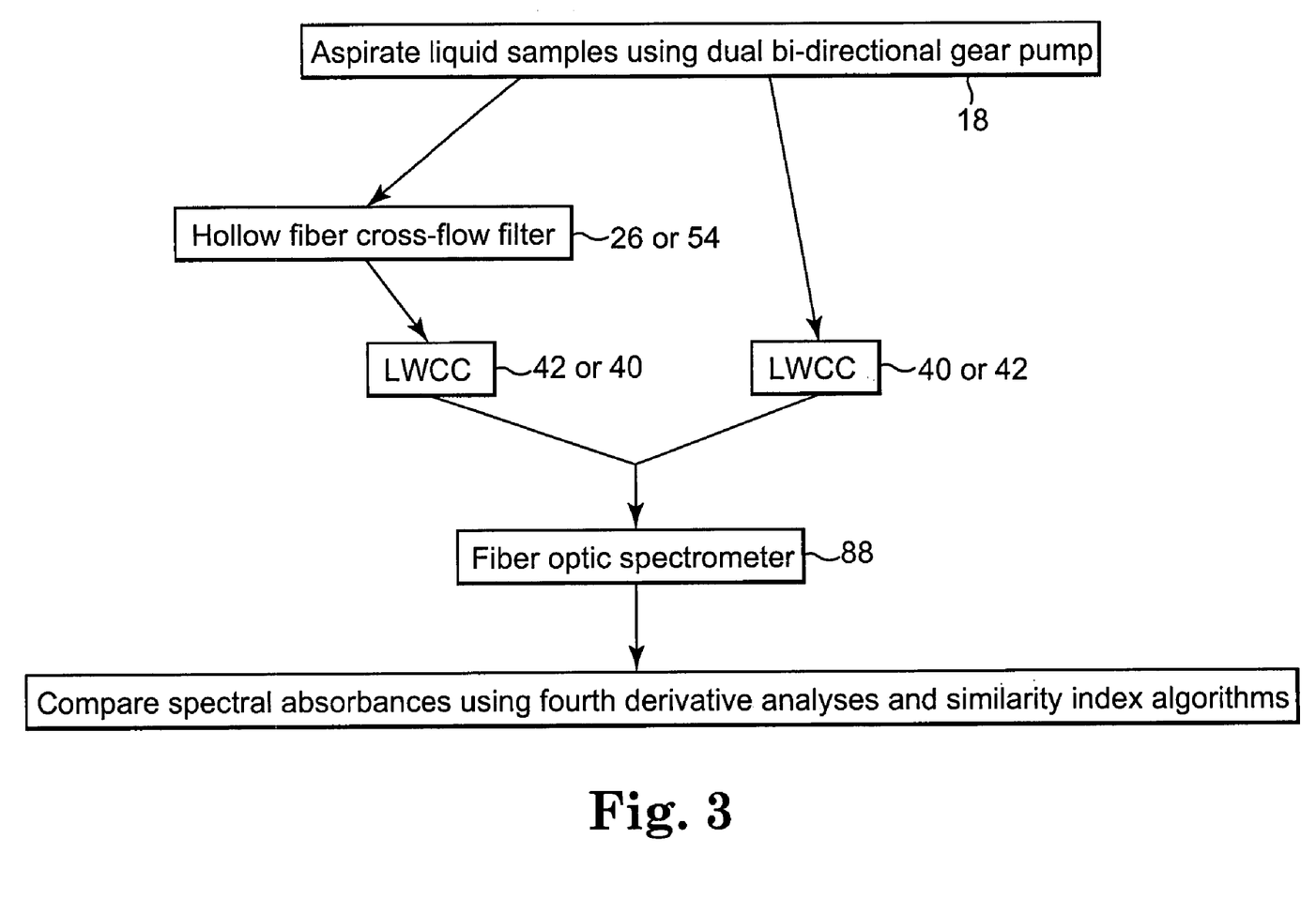
FIG. 3 is a flow chart illustrating operation of the FIG. 1 apparatus.

FIG. 3 is a flow chart showing several steps in the operation of apparatus 10. The liquid samples may be aspirated through apparatus 10 using pump 18. The aspiration volume may be controlled by operating motor 20 for a defined time period, and may be very small, e.g., about 250 microliters to 2 milliliters, or may be considerably larger. The ability to adjust the aspiration volume makes the disclosed apparatus more versatile and better suited for use in a variety of sampling situations. A first circuit in pump 18 supplies liquid to filter 26 and filtrate to LWCC 42, and a second circuit in pump 18 supplies unfiltered or less finely filtered liquid to LWCC 40. When motor 20 is reversed, the second pump 18 circuit supplies liquid to filter 54 and filtrate to LWCC 40, and the first pump 18 circuit supplies unfiltered or less finely filtered liquid to LWCC 42. Meanwhile, fiber optic spectrometer 88 collects transmitted spectral data from LWCCs 40 and 42. The collected data may be used for example to identify or map phytoplankton species or to characterize or map CDOM characteristics in liquid water samples or in aquatic systems. Several species of algae can be measured simultaneously, e.g., by programming several target algal species absorbance spectra into the apparatus. The disclosed apparatus and method are especially well suited for detecting and if need be providing early warning of the presence of *K. brevis* in natural, mixed phytoplankton communities or in laboratory cultures. The disclosed apparatus and method may rely in part on the high sensitivity of derivative analysis to uncover subtle characteristics in the curvature of the absorbance spectrum. The disclosed apparatus and method are especially well-suited for making continuous or a semi-continuous, automated, unattended measurements in fresh or salt water environments. Such measurement may be made by moving through a bed of varying analyte or via stationary analysis amidst moving water currents.

Fourth derivative analysis and similarity index algorithms may be used to determine the presence of various materials in the liquid samples. The similarity index is a ratio comparing absorbance spectra from unknown organisms in a sample to absorbance spectra of known target algal species. For example, a processing algorithm for phytoplankton absorbance spectra to detect the red tide dinoflagellate, *K. brevis*, has been described in Millie et al., "Detection of harmful algal blooms using photopigments and absorption signatures: A case study of the Florida red tide dinoflagellate, Gymnodinium breve", Limnol. Oceanogr. 42, 1240–1251 (1997). This algorithm evaluates the fourth derivative of the particulate absorbance spectrum of an unknown sample and compares it to a standard fourth derivative spectrum for *K. brevis*. Generally, the closeness of the curves is calculated using a ratio of several peaks in the spectra. Similarity indices greater than 0.7 are generally considered positive for the target organism. This algorithm may be used in the disclosed apparatus and method. Previous optical approaches to phytoplankton discrimination typically provide only bulk composite signals for a given water mass. Signatures for distinct phytoplankton species are difficult to discriminate. The disclosed apparatus and method can provide a useful field survey system capable of making spectral absorbance measurements and providing early warning to the presence of organisms including *K. brevis* in a variety of water and weather conditions including oligotrophic waters. The disclosed apparatus and method can also provide real-time automated CDOM measurement with greatly increased spatial and temporal sampling coverage compared to standard, discrete sampling methods. A high degree of variability in CDOM concentration exists in coastal waters and is difficult or impossible to resolve via traditional discrete CDOM sampling techniques. The disclosed apparatus can be used to obtain comprehensive three-dimensional views over time and space of CDOM absorption characteristics in large aquatic systems at both high and low CDOM or algal species levels.

Figure 4:
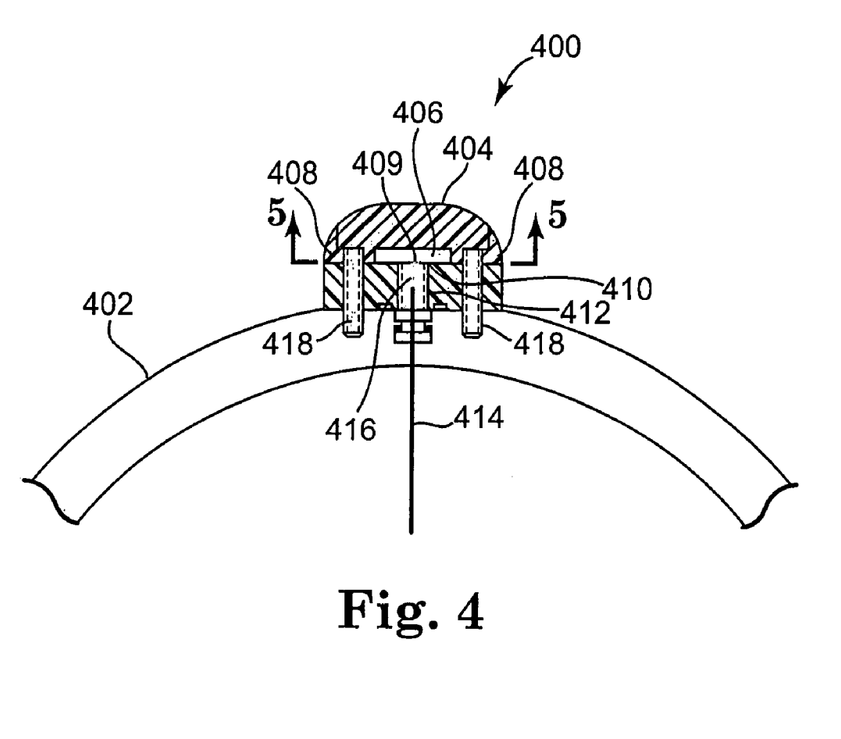
FIG. 4 is a cross-sectional view of a bidirectional port.

FIG. 4 shows a cross-sectional view of bidirectional port 400 mounted on a hull or other underwater housing 402. The outer cover 404 of port 400 may be made, for example, from clear or opaque plastic, with a machined or molded opening 406 that permits liquid to pass into port 400 and two machined or molded openings 408 that permit liquid to pass out of port 400. Desirably the liquid volume passing from opening 406 to openings 408 is much larger (e.g., several hundreds or thousands of times larger) than the liquid volume actually entering or exiting the disclosed apparatus, thereby helping to sweep port 400 clean and to assist in collecting accurate liquid samples. A perforated copper gasket 410 is situated directly over fitting 412 to discourage biofouling. Gasket 410 has a small opening 411 to permit liquid samples to pass into or out of the disclosed apparatus. When entering the disclosed apparatus, the sample passes through replaceable stainless steel mesh or size fractionation prefilter 416 situated in fitting 412, and thence through tubing 414 to the remainder of the disclosed apparatus inside housing 402. Prefilter 416 may have openings sized to permit algal cells of a target species of interest to pass through prefilter 416 while preventing larger cells or other large particles from being aspirated into the disclosed apparatus and obstructing its components. The openings in prefilter 416 may for example be sized at about 15 um to 100 um and desirably for detection of *K. brevis* may be sized at about 40 um. Port 400 may be attached to housing 402 using seawater-resistant fasteners 418.

Figure 5:
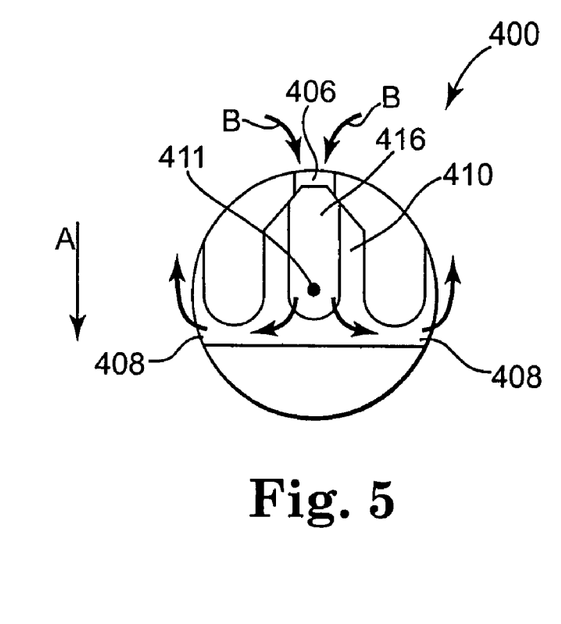
FIG. 5 is a plan sectional view of the FIG. 4 port showing water flowing past the port.

FIG. 5 shows bidirectional port 400 in a plan sectional view taken at line 5–5' in FIG. 4. The housing on which port 400 is mounted is moving in direction A. Due to the Bernoulli Effect, liquid (e.g., seawater) passes into port 400 via opening 406 as indicated generally by flow arrows B and passes out of port 400 via openings 408 as indicated generally by flow arrows C. So long as the motion indicated by arrow A continues at a sufficient rate, liquid will flow through port 400 as shown by arrows B and C whether port 400 is serving as an intake or an outlet for the disclosed apparatus. The liquid sample flowing into or out of the disclosed apparatus will however be reversible and when flowing outward will help keep port 400 free of debris.

Figure 6:
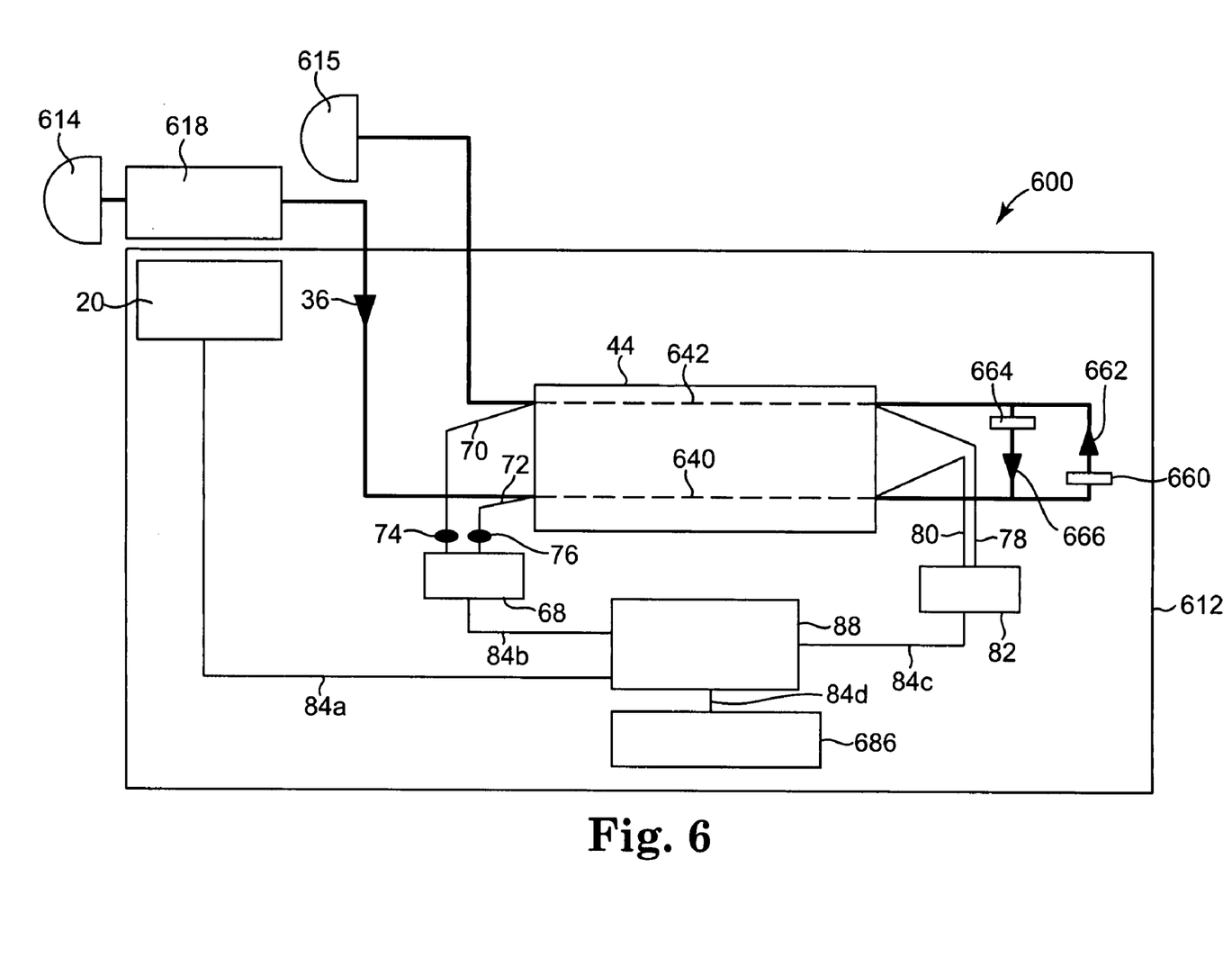
FIG. 6 is a schematic view of an Optical Phytoplankton Discriminator apparatus with series-connected LWCCs.

FIG. 6 is a schematic view of an Optical Phytoplankton Discriminator apparatus 600 with series-connected LWCCs 640 and 642 mounted inside housing 612. Liquids enter and leave apparatus 600 via first bidirectional port 614 and second bidirectional port 615. Port 614 is connected via suitable tubing to single channel bidirectional gear pump 618. When the liquid flow direction is such that port 614 is serving as an inlet, liquid exits pump 618 through suitable tubing and enters one end of LWCC 640. Liquid can exit the other end of LWCC 640 by traveling through removable inline stop-flow filter 660 and check valve 662 to one end of LWCC 642. Liquid can exit the other end of LWCC 642 and apparatus 600 through port 615. In this fashion different liquid samples are supplied to LWCCs 640 and 642, with LWCC 640 receiving an unfiltered or less finely filtered sample and LWCC 642 receiving a more finely filtered sample representing a filtering version of the sample exiting LWCC 640. The remaining components in FIG. 6 numbered like those in FIG. 1 have the same description and function as was given for FIG. 1. When pump 618 is reversed, the flow of liquid through apparatus 600 reverses, and liquid flows from LWCC 642 through filter 664 and check valve 666. The resulting liquid flow reversal can remove debris from ports 614 and 615 and from LWCCs 640 and 642. The apparatus shown in FIG. 6 may require more frequent filter replacement (and thus might be less well suited for unattended field use) than the apparatus shown in FIG. 1. However, the FIG. 6 apparatus may have particular utility for laboratory benchtop applications. The FIG. 6 apparatus should for example be less expensive to build and operate (particularly since it could employ relatively inexpensive filters) and may provide a more compact apparatus. It would also be useful when it is desired to save material collected on the filter for other applications such as quantitative measurement of the amount of collected material, pigment analyses, carrying out absorbance measurements directly in the spectrometer for calibration or other purposes, identification of species using molecular probes, and other applications that will be familiar to those skilled in the art.

The LWCCs in the disclosed apparatus may desirably be sufficiently like one another so that they will be "interchangeable", that is, so that these components may be used for reference sample measurements or discriminate sample measurements without materially adversely affecting the accuracy of the disclosed apparatus. More than two LWCCs may also be employed if desired in the disclosed apparatus. For example, the FIG. 1 parallel-connected LWCC circuit and FIG. 6 series-connected LWCC circuit could be combined in a single apparatus and the two circuits used together (e.g., with four LWCCs), or may be selected in the alternative using two LWCCs and suitable valves or other controls. Three or more LWCCs could be used in a single apparatus, and need not interchangeably analyze the same species. For example, samples could be supplied to two or more LWCCS and compared to yet another reference LWCC operating at the same time.

The liquid samples may be collected semi-continuously on a pre-determined schedule, e.g., every 15 minutes or another suitable interval, or may be collected continuously without any gaps in liquid intake through one or the other of the bidirectional ports. The frequency of CDOM reference and discriminate sample measurement may be adjusted if more frequent measurement of the reference or discriminate sample is desired. Also, more frequent sampling of one analyte compared to other analytes may also be carried out.

The disclosed apparatus and method can greatly reduce or can essentially eliminate data recording gaps caused by cleaning and new reference spectrum collection. Additionally, by operating two or more LWCCs simultaneously, the reference sample and discriminate sample will come from the same water, as opposed to coming from similar but at best nearby water samples. The disclosed apparatus may be adapted for use in an autonomous underwater vehicle, such as a buoyancy-driven underwater glider, vertical profiler, or a propeller-driven surveyor, for carrying out roving underwater analysis. Such analysis may for example be performed in or through a bed of varying analyte, thereby permitting continuous or semi-continuous, automated unattended sampling under conditions that might normally clog the apparatus with debris. The disclosed apparatus may also be moored or otherwise installed at a fixed maritime location such as a buoy, piling, marker, or other marine platform, and used to collect data over time (e.g., for several weeks) to allow continuous monitoring at a specific location. Suitably-constructed field models may be used under high pressure conditions such as sampling in deep water (e.g., for depths down to 50 or 60 meters or more) or under ambient pressure on a platform near the surface. Position information for such maritime devices may be obtained directly from a dedicated global positioning system interfaced to the onboard microcomputer and may be updated continuously or at surfacing intervals. The disclosed apparatus may also be adapted for use in a fixed onshore location, such as the above-mentioned benchtop model for analysis of liquid samples in a laboratory. Liquid samples can be introduced into such a benchtop model in a number of ways that will be apparent to those skilled in the art, including discrete injection and continuous sample flow.

Figure 7:
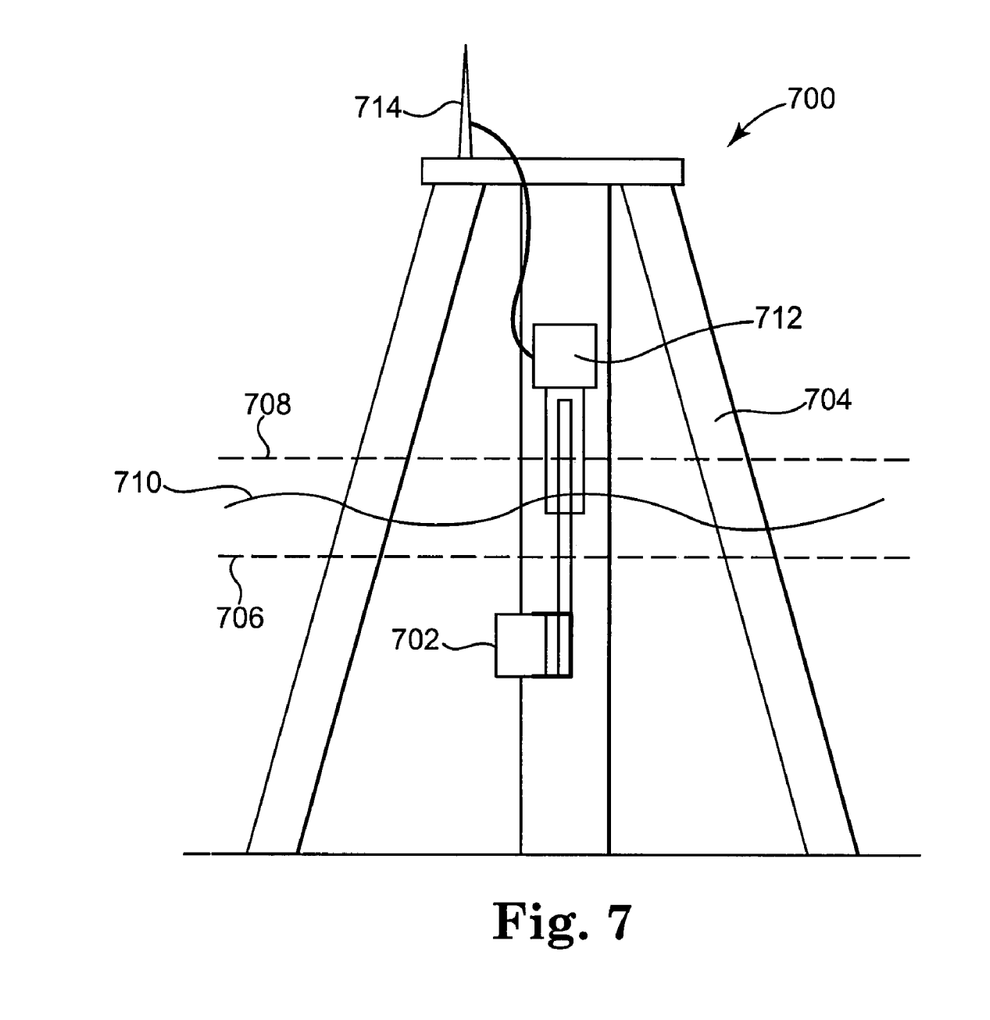
FIG. 7 is a schematic view of an Optical Phytoplankton Discriminator mounted on a mooring or buoy.

FIG. 7 shows an Optical Phytoplankton Discriminator 700 encased in watertight underwater instrument housing 702 attached to channel marker 704. Housing 702 desirably is positioned a suitable distance below the mean low water mark 706 (e.g., at least 30 cm below mean low water mark 706) so that normal wave action 710 will not expose the bidirectional ports (not shown in FIG. 7) in housing 702. A wireless modem and battery box 712 connected to housing 702 desirably is positioned a suitable distance above mean high water mark 708 so that it normally remains unimmersed. An antenna 714 placed atop marker 704 enables data to be transmitted from (or if need be, to) Optical Phytoplankton Discriminator 700.

Various modifications and alterations of this invention will be apparent to those skilled in the art without departing from this invention. This invention should not be restricted to that which has been set forth herein only for illustrative purposes.

The invention claimed is:

1. An apparatus for analyzing liquid samples, the apparatus comprising:
    (a) first and second bidirectional ports for providing liquid samples to the apparatus and discharging liquid samples from the apparatus,
    (b) first and second liquid waveguide capillary cells in fluid communication with the first and second ports and arranged to analyze different liquid samples at the same time,
    (c) at least one light source and at least one spectrometer in optical communication with the first and second cells, and
    (a) a bidirectional pump or control arranged to flow samples in alternate directions through the first and second ports.

2. An apparatus according to claim 1 wherein the first and second ports are each in fluid communication with one of the first and second cells and in filtered fluid communication with the other of the first and second cells.

3. An apparatus according to claim 1 wherein the cells are interchangeable.

4. An apparatus according to claim 1 wherein the cells are arranged in parallel.

5. An apparatus according to claim 1 wherein the cells are arranged in series.

6. An apparatus according to claim 1 which carries out continuous sample analysis.

7. An apparatus according to claim 1, further comprising a shutter to supply light to a cell in intermittent fashion.

8. An apparatus according to claim 7, wherein a shutter or shutters supply light to the first and second cells in alternating fashion.

9. An apparatus according to claim 1 capable of roving analysis in an autonomous underwater vehicle.

10. An apparatus according to claim 1 capable of continuous monitoring over time at a fixed maritime platform.

11. An apparatus according to claim 1 capable of benchtop analyses in a laboratory.

12. A method for analyzing liquid samples comprising:
    (a) obtaining one or more liquid samples through a first bidirectional port,
    (b) flowing the sample(s) into two or more liquid waveguide capillary cells,
    (c) spectroscopically analyzing the contents of the cells,
    (d) discharging the sample(s) through a second bidirectional port,
    (e) reversing the sample flow direction through the first and second ports, and (f) repeating steps (b) and (c) using such reversed sample flow.

13. A method according to claim 12, comprising semi-continuously spectroscopically analyzing the contents of the cells.

14. A method according to claim 12, comprising continuously spectroscopically analyzing the contents of the cells.

15. A method according to claim 12, wherein reversing the sample flow direction reverses the cell role and flow direction.

16. A method according to claim 12, wherein reversing the sample flow direction prevents or discourages debris from obstructing the ports.

17. A method according to claim 12, wherein two or more samples are obtained and one sample is obtained more frequently than other samples.

18. A method according to claim 12, wherein the samples are obtained in an automated, unattended fashion.

19. A method according to claim 12, wherein the samples are obtained by roving underwater analysis through a bed of varying analyte.

20. A method according to claim 12, wherein the samples are obtained by continuous monitoring over time at a fixed maritime platform.

* * * * *